United States Patent
Lannert

[11] 3,970,698
[45] July 20, 1976

[54] HYDROXY ETHER CARBOXYLATES

[75] Inventor: Kent P. Lannert, Freeburg, Ill.

[73] Assignee: Monsanto Company, St. Louis, Mo.

[22] Filed: Dec. 19, 1973

[21] Appl. No.: 426,296

[52] U.S. Cl............ 260/535 P; 252/89 R; 252/99; 252/132; 252/135; 252/535; 252/539; 252/DIG. 11; 260/484 P; 260/501.15; 260/501.17

[51] Int. Cl.² .............. C07C 59/22; C07C 69/66

[58] Field of Search........ 260/535 P, 484 P, 501.15, 260/501.17

[56] References Cited
FOREIGN PATENTS OR APPLICATIONS
2,248,708  4/1973  Germany.......................... 260/535 P OTHER PUBLICATIONS
Walker, J. F., Formaldehyde, Reinhold Publishing Co., N.Y., 1944, p. 109.

*Primary Examiner*—Paul J. Killos
*Attorney, Agent, or Firm*—N. E. Willis; J. E. Maurer; T. N. Wallin

[57] ABSTRACT

Hydroxy ether carboxylates represented by the formula

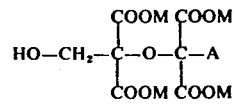

wherein M is alkali metal, ammonium, alkyl ammonium or alkanol ammonium and A is hydrogen, methyl, ethyl, or $CH_2OH$, are useful as complexing agents and detergency builders. The ester and acid forms of such compounds are useful as intermediates for preparation of the salts.

3 Claims, No Drawings

HYDROXY ETHER CARBOXYLATES

BACKGROUND OF THE INVENTION

This invention relates to novel hydroxy ether carboxylate salts useful as complexing agents and detergency builders, to ester and acid forms of such compounds useful as intermediates for preparation of the salts, to methods of preparing the ester, acid and salt compounds, and to detergent formulations containing the salt compounds.

The utility of compounds characterized by the ability to complex various metal and alkaline earth metal ions (particularly ions such as calcium ions which contribute to "hardness" of water) in aqueous media and/or provide, in combination with various detergent surfactants, detergent formulations of enhanced cleansing ability is well recognized by those skilled in the art. Such compounds are used in water treating applications (e.g. to "soften" water) and/or as detergency builders.

Although many compounds having complexing and/or detergency builder functionality are known, the provision of novel compounds composed of only carbon, hydrogen and oxygen and having such functionality is desirable.

SUMMARY OF THE INVENTION

It is an object of this invention to provide novel compounds useful as complexing agents and/or detergency builders and intermediates for the synthesis of such compounds.

The compounds of this invention are hydroxy ether polycarboxylic acids, salts and esters whose structure, synthesis, and use will be understood from the following description of the preferred embodiments.

DESCRIPTION OF THE PREFERRED EMBODIMENTS

The compounds of the present invention are represented by the formula

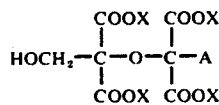

wherein X is hydrogen, alkyl containing from 1 to 20 carbon atoms, alkali metal, ammonium, alkyl ammonium containing from 1 to 4 carbon atoms or alkanol ammonium containing from 1 to 4 carbon atoms and A is hydrogen, methyl, ethyl or CH$_2$OH.

The ester and acid forms of the compounds of this invention are useful as intermediates for preparation of the salt forms as will be apparent from the description of methods of preparing compounds of this invention.

The ester forms of the compounds of this invention are prepared by reacting an ether carboxylate ester represented by the formula

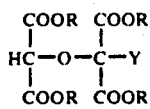

(wherein R is an alkyl group containing from 1 to 20 carbon atoms and Y is hydrogen, methyl or ethyl) with formaldehyde.

The formaldehyde can be provided directly or materials capable of providing formaldehyde under reaction conditions (e.g. paraformaldehyde, trioxane) can be utilized. Methanol stabilized aqueous formaldehyde solutions (formalin) provide a particularly convenient source of formaldehyde.

The reaction is conducted in a medium sufficiently basic to deprotonate but not so basic as to substantially (more than 30%) hydrolyze or saponify the ether carboxylate ester. This degree of basicity is conveniently obtained with a weak base such as potassium bicarbonate. Preferred reaction temperatures are in the range of 15°C to 30°C although higher or lower temperatures (generally in the range of 5°C to 200°C) can be utilized if desired. At higher temperatures, appropriate pressure or reflux means are desirably employed.

The starting ether carboxylate esters can be prepared from diethyl diglycolate, diethyl methyldiglycolate or diethyl ethyldiglycolate which are, respectively, prepared by adding ethyl glycolate, ethyl lactate, or ethyl 2-hydroxybutyrate to sodium hydride slurried in tetrahydrofuran cooled to about 15°C and adding ethyl bromoacetate. The diglycolate product is recovered by evaporating solvent, washing the residue with water to remove salts, drying and distillation.

The diglycolate in tetrahydrofuran solution is added (at about −75°C) to a mixture formed by adding n-butyllithium to a tetrahydrofuran solution of diisopropylamine.

It is believed that this procedure results in formation of a lithium salt represented by the formula

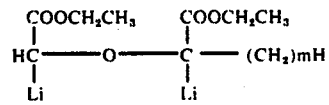

($m$ is an integer from 0 to 2.)

Gaseous CO$_2$ is then introduced to form

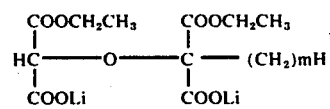

which is dissolved in water and converted to a half-ester half-acid:

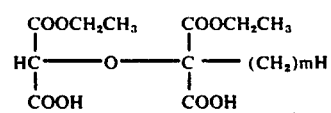

by treatment with a strong acid ion exchange resin (e.g. a sulfonated polystyrene resin such as marketed by Fischer Scientific Company under the trademark Rexyn 101).

The half-ester half-acid is completely esterified by dissolving in ethyl alcohol and benzene and acidifying with concentrated sulfuric acid in accordance with conventional esterification practice. The acid forms of the starting ether carboxylate esters can be obtained by conventional techniques (e.g. saponification followed by acidulation) and used to prepare higher ester starting materials, if desired.

If the starting ester

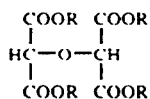

is reacted with amounts of formaldehyde less than stoichemetric for formation of

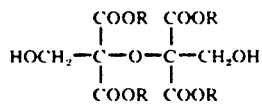

a mixture of this material with

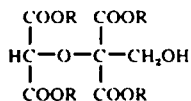

will be obtained. This mixture (or acids or salts thereof) can be used as such or the individual compounds can be isolated by conventional techniques.

The corresponding alkali metal salt forms of the compounds of this invention are readily obtained by conventional saponification techniques. The corresponding ammonium and alkanol ammonium salts are more easily obtained by neutralization of the acid forms of the compounds of this invention.

Acidulation of the salt with a strong acid, e.g., HCl, $H_2SO_4$, or a strong acid ion exchange resin, will yield the acid forms of the compounds of this invention.

The hydroxyether polycarboxylate salts of this invention are useful as agents for complexing metal and/or alkaline earth metal ions in aqueous media. The amount of polycarboxylate required to effectively complex the ions in a given system will depend, to some extent, on the particular polycarboxylate salt being used and the particular metal or alkaline earth metal ions in the aqueous media. Generally, complexing is more effective in basic solution. Optimum conditions and amounts of complexing agent can readily be determined by routine experimentation.

The hydroxy ether polycarboxylate salts are also useful as builders in detergent formulations. Generally, the use of the alkali metal salts, particularly the sodium salt is preferred. However, in some formulations (such as liquid formulations where greater builder solubility is required) the use of ammonium or alkanol ammonium salts may be desirable.

The detergent formulations will contain at least 1% by weight and preferably at least 5% by weight of the hydroxy ether polycarboxylate salts of this invention. In order to obtain the maximum advantages of the builder compositions of this invention, the use of from 5% to 75% of these polycarboxylate salts is particularly preferred. The hydroxy ether polycarboxylate salt compounds of this invention can be the sole detergency builder or these compounds can be utilized in combination with other detergency builders which may constitute from 0 to 95% by weight of the total builders in the formulation. By way of example, builders which can be employed in combination with the novel builder compounds of this invention include water soluble inorganic builder salts such as alkali metal polyphosphates, i.e., the tripolyphosphates and pyrophosphates, alkali metal carbonates, borates, bicarbonates and silicates and water soluble organic builders including amino polycarboxylic acids and salts such as alkali metal nitrilotriacetates, cycloalkane polycarboxylic acids and salts, ether polycarboxylates (for example, the salt forms of the esters reacted to prepare the ester forms of the compounds of the present invention), alkyl polycarboxylates, epoxy polycarboxylates, tetrahydrofuran polycarboxylates such as 1,2,3,4 or 2,2,5,5 tetrahydrofuran tetracarboxylates, benzene polycarboxylates, oxidized starches, amino (trimethylene phosphonic acid) and its salts, diphosphonic acids and salts (e.g., methylene diphosphonic acid; 1-hydroxy ethylidene diphosphonic acid) and the like.

The detergent formulations will generally contain from 5% to 95% by weight total builder (although greater or lesser quantities may be employed if desired) which, as indicated above, may be solely the hydroxy ether polycarboxylate salt compounds of this invention or mixtures of such compounds with other builders. The total amount of builder employed will be dependent on the intended use of the detergent formulation, other ingredients of the formulation, pH conditions and the like. For example, general laundry powder formulations will usually contain 20% to 60% builder, liquid dishwashing formulations 11% to 12% builder; machine dishwashing formulations 60% to 90% builder. Optimum levels of builder content as well as optimum mixtures of builders of this invention with other builders for various uses can be determined by routine tests in accordance with conventional detergent formulation practice.

The detergent formulations wll generally contain a water soluble detergent surfactant although the surfactant ingredient may be omitted from machine dishwashing formulations. Any water soluble anionic, nonionic, zwitterionic or amphoteric surfactant can be employed.

Examples of suitable anionic surfactants include soaps such as the salts of fatty acids containing about 9 to 20 carbon atoms, e.g. salts of fatty acids derived from coconut oil and tallow; alkyl benzene sulfonates—particularly linear alkyl benzene sulfonates in which the alkyl group contains from 10 to 16 carbon atoms; alcohol sulfates; ethoxylated alcohol sulfates; hydroxy alkyl sulfonates; alkenyl and alkyl sulfates and sulfonates; monoglyceride sulfates; acid condensates of fatty acid chlorides with hydroxy alkyl sulfonates and the like.

Examples of suitable nonionic surfactants include alkylene oxide (e.g., ethylene oxide) condensates of mono and polyhydroxy alcohols, alkyl phenols, fatty acid amides, and fatty amines; amine oxides; sugar derivatives such as sucrose monopalmitate; long chain tertiary phosphine oxides; dialkyl sulfoxides; fatty acid amides, (e.g., mono or diethanol amides of fatty acids containing 10 to 18 carbon atoms), and the like.

Examples of suitable zwitterionic surfactants include derivatives of aliphatic quaternary ammonium compounds such as 3-(N,N-dimethyl-N-hexadecyl ammonio) propane-1-sulfonate and 3-(N,N-dimethyl-N-hexadecyl ammonio)-2-hydroxy propane-1-sulfonate.

Examples of suitable amphoteric surfactants include betains, sulfobetains and fatty acid imidazole carboxylates and sulfonates.

It will be understood that the above examples of surfactants are by no means comprehensive and that numerous other surfactants are known to those skilled in the art. It will be further understood that the choice and use of surfactants will be in accordance with well understood practices of detergent formulation. For example, anionic surfactants, particularly linear alkyl benzene sulfonate are preferred for use in general laundry formulations, whereas low foaming nonionic surfactants are preferred for use in machine dishwashing formulations.

The quantity of surfactant employed in the detergent formulations will depend on the surfactant chosen and the end use of the formulation. In general, the formulations will contain from 5% to 50% surfactant by weight, although as much as 95% or more surfactant may be employed if desired. For example, general laundry powder formulations normally contain 5% to 50%, preferably 15% to 25% surfactant; machine dishwashing formulations 0.5% to 5%; liquid dishwashing formulations 20% to 45%. The weight ratio of surfactant to builder will generally be in the range of from 1:12 to 2:1.

In addition to builder and surfactant components, detergent formulations may contain fillers such as sodium sulfate and minor amounts of bleaches, dyes, optical brighteners, soil anti-redeposition agents, perfumes and the like.

In machine dishwashing compositions the surfactant will be a low-foaming anionic or preferably, nonionic surfactant which will constitute 0 to 5% of the formulation.

The term "low-foaming" surfactant connotes a surfactant which, in the foaming test described below, reduces the revolutions of the washer jet-spray arm during the wash and rinse cycles less than 15%, preferably less than 10%.

In the foaming test, 1.5 grams of surfactant is added to a 1969 Kitchen-Aid Home Dishwasher, Model No. KOS-16, manufactured by Hobart Manufacturing Company which is provided with means for counting revolutions of the washer jet-spray arm during wash and rinse cycles. The machine is operated using distilled water feed at a machine entrance temperature of 40°C. The number of revolutions of the jet-spray arm during the wash and rinse cycles is counted. The results are compared with those obtained by operation of the machine using no surfactant charge and the percentage decrease in the number of revolutions is determined.

The surfactant should, of course, be compatible with the chlorine containing component hereinafter discussed. Examples of suitable nonionic surfactants include ethoxylated alkyl phenols, ethoxylated alcohols (both mono- and di- hydroxy alcohols), polyoxyalkylene glycols, aliphatic polyethers and the like. The widely commercially utilized condensates of polyoxypropylene glycols having molecular weights of from about 1400 to 2200 with ethylene oxide (the ethylene oxide constituting 5 to 35 weight percent of the condensate) are, for example, advantageously used in the machine dishwashing formulations of this invention.

Suitable low-foaming anionic surfactants include alkyl diphenyl ether sulfonates such as sodium dodecyl diphenyl ether disulfonates and alkyl naphthalene sulfonates.

Mixtures of suitable low-foaming surfactants can be utilized if desired.

In addition, machine dishwashing formulations will contain sufficient chlorine providing compound to provide 0.5% to 2% available chlorine. For example, the formulation may contain from 0.5% to 5%, preferably 1% to 3% of a chlorocyanurate or from 10% to 30% chlorinated trisodium phosphate. Suitable chlorocyanurates are sodium and potassium dichlorocyanurate; [(monotrichloro) tetra-(monopotassium dichloro)] penta-isocyanurate; (monotrichloro) (monopotassium dichloro) diisocyanurate.

Machine dishwashing compositions should additionally contain from 5% to 30% soluble sodium silicate having an $SiO_2$ to $Na_2O$ mole ratio of from 1:1 to 3.2:1 preferably about 2.4:1 to inhibit corrosion of metal parts of dishwashing machines and provide over-glaze protection to fine china.

Machine dishwashing compositions will generally contain at least 10%, preferably at least 20% builder, up to a maximum of about 90% builder. The new builder compounds of this invention should constitute at least 5% of the weight of the machine dishwashing formulation in order to obtain the full effects of their inherent characteristics.

EXAMPLE I

Diethyl diglycolate is prepared by slurrying 270 parts sodium hydride in 2800 parts tetrahydrofuran and adding 705 parts ethyl glycolate to the mixture while maintaining the temperature between 10° to 15°C. The mixture is stirred for 1 hour at 25°C, cooled to 15°C and 894 parts ethyl bromoacetate is added. The mixture is stirred for 12 hours at 25°C; solvent evaporated; residue washed with water to remove salts; dried and purified diethyl digylcolate recovered by distillation under reduced pressure. (Note: Diethyl methylglycolate or diethyl ethyldiglycolate are prepared by similar procedures wherein ethyl lactate (800 parts) or ethyl-2-hydroxybutyrate (895 parts) are, respectively, substituted for the ethyl glycolate.)

A solution of 21 parts diethyl diglycolate in 100 parts tetrahydrofuran is added to a mixture prepared by adding 115 parts 2.3 molar n-butyl lithium to a solution of 24 parts diisopropylamine in 400 parts tetrahydrofuran cooled to −30°C. The resulting mixture is allowed to warm to −10°C for about 10 minutes and then cooled to −75°C. A solution of 21 parts diethyl diglycolate in 100 parts tetrahydrofuran is added while maintaining the temperature below −70°C.

Gaseous $CO_2$ is passed through the mixture which is maintained at −45°C to −75°C for 1 hour. The temperature is then allowed to rise to 25°C while maintaining $CO_2$ flow.

Tetrahydrofuran is evaporated leaving a residue which is dissolved in water and passed through a strong acid ion exchange column (packed with a sulfonated polystyrene resin marketed by Fischer Scientific Company under the trademark Rexyn 101).

High vacuum evaporation of the water leaves a thick syrup-like residue which is completely esterified to form tetraethyl oxydimalonate by dissolving in 25 parts ethanol, 40 parts benzene and 0.2 parts concentrated sulfuric acid; azeotropically removing water; adding 3 parts additional ethanol; distilling off excess alcohol and benzene. The residue is dissolved in benzene; washed with 5% $NaHCO_3$ and water; dried over MgSO₄; stripped of benzene by evaporation and distilled. The tetraethyl oxydimalonate is collected in the range of 141° to 143°C, 0.05 mm. Hg. (Note: tetraethyl 2-methyl oxydimalonate or tetraethyl 2-ethyl oxydimalonate can be prepared by similar procedures in which diethyl methyldiglycolate or diethyl ethyldiglycolate is substituted for the diethyl diglycolate.)

The tetraethyl oxydimalonate (34 parts) is added to a rapidly stirred solution of 2 parts KHCO₃ dissolved in 33 parts formalin (37% formaldehyde). The temperature is maintained between 35° to 40°C during the slightly exothermic reaction which yields tetraethyl 2,2'-bis(hydroxymethyl)oxydimalonate

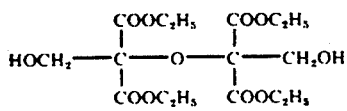

Addition of 70 parts, 25% NaOH aqueous solution saponifies the ester to tetrasodium 2,2'-bis(hydroxymethyl)oxydimalonate

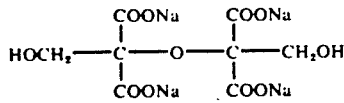

which is separated by addition of excess methanol. The salt is purified by dissolving in water; adding ethanol to separate an oil which is triturated in acetone to give the product as a granular white powder.

The tetrasodium 2,2'-bis(hydroxymethyl)oxydimalonate has a hydrogen nuclear magnetic resonance spectrum (determined in deuterium oxide) exhibiting singlets at about 5 ppm (OH protons of the methylol groups) and at about 4.3 ppm (CH₂ protons).

EXAMPLE II

Tetrasodium 2,2'-bis(hydroxymethyl)oxydimalonate is tested for sequestration function using the procedures described by Matzner et al, "Organic Builder Salts as Replacements for Sodium Tripolyphosphate", *Tenside Detergents*, 10, Heft 3, pages 119-125 (1973).

The sequestration value (intensity multiplied by capacity expressed as a percentage of sodium tripolyphosphate sequestration value) of tetrasodium 2,2'-bis(hydroxymethyl)-oxydimalonate is 127%.

EXAMPLE III

Detergent formulations containing the percent builder shown in Table I below; 17% linear alkylbenzene sulfonate having an average molecular weight of about 230; 6% sodium silicate; remainder, sodium sulfate are prepared. The formulations are tested by washing identically soiled fabric swatches (indicated in the table) in water of 200 ppm hardness at 49°C containing 0.15% detergent formulation using identical washing techniques. The reflectivity of the soiled swatches before and after washing is measured instrumentally and the difference reported in Table I as Δ Rd. High Δ Rd values are indicative of correspondingly high detergency effectiveness.

TABLE I

| Builder | Cotton Fabric ΔRd % Builder | | | Polyester/Cotton Fabric Δ Rd % Builder | | |
|---|---|---|---|---|---|---|
| | 50 | 37.5 | 25 | 50 | 37.5 | 25 |
| none (a filler-sodium sulfate-is used in place of builder) | <13 | <13 | <13 | <5 | <5 | <5 |
| tetrasodium 2,2'-bis(hydroxymethyl)oxydimalonate | 29.2 | 18.1 | 13.8 | 9.1 | 8.6 | 5.4 |

The data presented in Table I show the salt forms of the compounds of this invention to be effective detergency builders.

What is claimed is:
1. Compounds represented by the formula

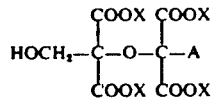

wherein A is selected from the group consisting of hydrogen, methyl, ethyl and —CH₂OH and X is selected from the group consisting of hydrogen, alkali metal, ammonium, alkyl ammonium containing 1 to 4 carbon atoms alkanol ammonium containing 1 to 4 carbon atoms, and alkyl groups containing 1 to 20 carbon atoms.

2. Compounds according to claim 1 wherein X is sodium.

3. Compounds according to claim 1 wherein A is CH₂OH.

* * * * *